United States Patent [19]

Von Behren

[11] Patent Number: 4,458,688

[45] Date of Patent: Jul. 10, 1984

[54] METHOD AND APPARATUS FOR CARDIAC NUCLEAR IMAGING

[75] Inventor: Patrick L. Von Behren, Hoffman Estates, Ill.

[73] Assignee: Siemens Gammasonics, Inc., Des Plaines, Ill.

[21] Appl. No.: 395,735

[22] Filed: Jul. 6, 1982

[51] Int. Cl.³ .................... G06F 15/42; G01N 23/04; A61B 6/00; G01T 1/164
[52] U.S. Cl. .................................. 128/659; 364/414; 378/901
[58] Field of Search ............... 128/653, 659; 358/111; 364/413, 414; 378/901; 382/6; 250/363 S

[56] References Cited

U.S. PATENT DOCUMENTS

| | | |
|---|---|---|
| 3,011,057 | 11/1961 | Anger. |
| 3,297,896 | 1/1967 | Anton .................................. 128/659 |
| 3,983,398 | 9/1976 | Boyd ................................... 378/901 |
| 4,068,306 | 1/1978 | Chen et al. .......................... 378/901 |
| 4,149,249 | 4/1979 | Pavkovich ........................... 378/901 |
| 4,182,311 | 1/1980 | Seppi et al. ......................... 128/653 |
| 4,212,062 | 7/1980 | Kohno et al. ....................... 364/414 |
| 4,298,944 | 11/1981 | Stoub et al. ....................... 250/363 S |
| 4,375,671 | 3/1983 | Engle .................................. 364/414 |
| 4,394,738 | 7/1983 | Wagner ............................... 364/414 |

OTHER PUBLICATIONS

Strauss et al., "Cardiac Nuclear Imaging: Principles, Instrumentation and Pitfalls", *Am. J. Cardiology,* Dec. 18, 1980, vol. 46, pp. 1109–1115.
Leitl et al., "Monitoring Cardiac Function With Nuclear Techniques", *Am. J. Cardiology,* Dec. 18, 1980, vol. 46, pp. 1125–1132.
Bodenheimer et al., "Nuclear Cardiology. I. Radionuclide Angiographic Assessment of Left Ventricular Contraction: Uses, Limitations and Future Directions, *Am. J. Cardiology,* Mar. 1980, vol. 45, pp. 661–673.
Nickel et al., "Image Analysis of the Heart Action Recorded with a High Speed Multicrystal Gamma Camera", *Medical Progress Through Technology,* vol. 5, No. 4 (1978).
"Data Processing and Functional Imaging in Radionuclide Ventriculography", H. Geffers, W. E. Adams, F. Bitter et al., *Proceedings of Fifth International Conference on Review of Information Processing in Medical Imaging,* TN 1977.
"Nuclear Medical Imaging", 8045 IEEE Spectrum, pp. 33–37, vol. 18 (1981) Jul., No. 7, New York, USA.
"Journal of Nuclear Medicine", vol. 18, No. 1, pp. 79–84, 1977 by Bacharach, Green, Borer, Douglas, Ostrow and Johnston.

*Primary Examiner*—William E. Kamm
*Assistant Examiner*—Mitchell J. Shein
*Attorney, Agent, or Firm*—Karl F. Milde, Jr.

[57] ABSTRACT

Counts of a gamma camera, acquired during a nuclear cardiac structure examination, which represent time-activity curves at different locations of a pixel matrix of the cardiac structure are fitted to a cosine wave function. From said fitted function the wave amplitude, phase, and an error value (representing the reliability of the acquired time-activity curve) are extracted. Finally, for each location in the pixel matrix said extracted values are simultaneously displayed as they are acquired.

6 Claims, 4 Drawing Figures

METHOD AND APPARATUS FOR CARDIAC NUCLEAR IMAGING

BACKGROUND OF THE INVENTION

1. Field of the Invention

This invention relates to a method and an apparatus for displaying images of a cardiac structure in nuclear examinations. Still more particularly, this invention relates to a method and an apparatus applied to radionuclide angiographic assessment of the heart and particularly the left ventricle. Still more particularly, this invention relates to diagnosis of heart motion by means of a gamma camera.

2. Description of the Prior Art

Radionuclide angiography has been increasingly utilized to evaluate cardiac structures and, in particular, left ventricular function in a wide variety of disease states.

Generally stated, to measure cardiac structure or function with nuclear techniques, the following procedure is followed: A radio-labeled tracer or radionuclide is administered to the patient and distributed in the heart in proportion to the function under investigation. Photons resulting from the decay of the radiotracer are collected by a scintillation camera. This scintillation camera contains a collimator which allows the photons arising only from specific areas of the heart to pass therethrough and to enter a scintillation crystal. In the scintillation crystal the photons interact to cause flashes of light. These light flashes are detected by photomultiplier tubes. Electric signals are transmitted to the scintillation camera electronics where the location of the interactions with the scintillation crystal is determined. Thus, the camera converts the gamma photon energy into an electrical signal that can be processed and displayed. The processed signal is transmitted to a computer system where it is stored and displayed on a screen. The computer is programmed to record the information and permit quantification and optimal display of the data. When the signals from a series of these interactions have been processed and displayed, the information forms a nuclear image.

The design of a specific scintillation camera, namely the Anger-type camera, is disclosed in U.S. Pat. No. 3,011,057, and details of cardiac nuclear imaging are described in "The American Journal of Cardiology", vol. 45, March 1980, pp. 661–673, vol. 46, December 1980, pp. 1109–1115, and vol. 46, December 1980, pp. 1125–1132.

In radionuclide cineangiography, a Fourier analysis technique was suggested in order to obtain images from acquired cardiac data (Geffers H., Adams W. E., Bitter F., et al.: Data Processing and Functional Imaging in Radionuclide Ventriculography; Proceedings of Fifth International Conference on Review of Information Processing in Medical Imaging, Nashville, TN, 1977).

In this previous approach the time activity curves (counts plotted versus time) for all single pixels are subject to a Fourier analysis. In this Fourier analysis, a Fast Fourier Transform (FFT) computer program is applied to each time-activity curve and used to evaluate or extract the amplitude A and phase $\phi$ of the fundamental frequency of the heart cycle. The amplitudes A and the phases $\phi$ are imaged for all pixels. Yet, there are some shortcomings. Fourier analysis techniques require (a) data which span a full cycle of the fundamental frequency, and the practical application via the FFT computer program requires (b) the number of sampled points to be a power of two. The first requirement (a) is difficult to achieve when there is a data drop-out in the time-activity curves due to variations of the R—R interval. To insure the second requirement (b), extra data manipulation is usually needed. A third shortcoming of the Fourier technique is that the fundamental period is not easily varied to match the "natural" heart period. Often, there is a period of diastis in the volume curve which causes the average R—R interval and the "natural" heart period to differ significantly. The fundamental period in the Fourier case is, by necessity, the R—R interval.

Even though the parameters A and $\phi$ are valuable tools in evaluating the amount of heart motion and the point of time when such motion occurs, there is no indication for the observing physician how reliable these parameters A and $\phi$ are.

SUMMARY OF THE INVENTION

Objects

An object of this invention is to provide a method for displaying nuclear images in order to obtain a reliable diagnosis of a cardiac structure.

It is another object of this invention to improve the quantification of cardiac motion by means of imaging the A and $\phi$ parameters in nuclear images of a cardiac structure.

It is still another object of this invention to improve the confidence of a physician in the displayed nuclear images of parameters of the heart.

It is still another object of this invention to give an indication of how reliable the measured and/or displayed parameters are to the observer of cardiac nuclear images.

Summary

In accordance with this invention, images of a cardiac structure are displayed by means of nuclear examination means. A radio-labeled tracer which is administered to a patient is distributed in the cardiac structure. By aid of a gamma camera, cardiac data are acquired in accordance with the local distribution of the tracer. Each of these data represents a time-activity curve at a certain location of a pixel matrix. This pixel matrix overlies the cardiac structure.

The time-activity curve contains the radiation counts as a function of time. The acquired cardiac data are stored in a memory which preferably is a portion of a computer such as a microprocessor.

By means of the computer, each of the time-activity curves is fitted to a cosine wave of the form.

$$c(t) = A_o + A \cos(2\pi t/T + \phi), \qquad (1)$$

wherein $A_o$ is the average value of the fitted cosine wave c(t), wherein A is the amplitude of the cosine wave c(t), wherein T is the period of the cosine wave c(t), and wherein $\phi$ is the phase of the cosine wave c(t).

From this fitted cosine wave c(t), the amplitude A, the phase $\phi$ and an error value E are extracted. The error value E represents the reliability of the acquired time-activity curve.

Preferably, a standard mathematical technique such as "a least square fitting" is applied to the fitting of the sinusoidal time-activity curve of each single pixel.

For each location or pixel, there may be simultaneously displayed the amplitude A, the phase $\phi$, and the error value E. The amplitude A and the phase $\phi$ render a first and second functional image, respectively. The image of the error values E of the individual pixel is indicative of the reliability of the individual amplitude and phase values A and $\phi$, respectively, contained in the first and second functional image, respectively. In another embodiment, the error value E may be compared with a predetermined maximum error value. Subsequently there is displayed for each location a parameter A and/or $\phi$ extracted from the fitted cosine wave when the error value E is smaller than the predetermined maximum error value. If the error value E is larger than the predetermined maximum error value, the parameter A and/or C of this pixel is rejected. Thus, the first and second functional images contain only data with proven reliability.

The foregoing and other objects, features and advantages of the invention will be apparent from the following more particular description of preferred embodiments of the invention, as illustrated in the accompanying drawings.

DETAILED DESCRIPTION OF THE PREFERRED EMBODIMENTS

Figure 1:
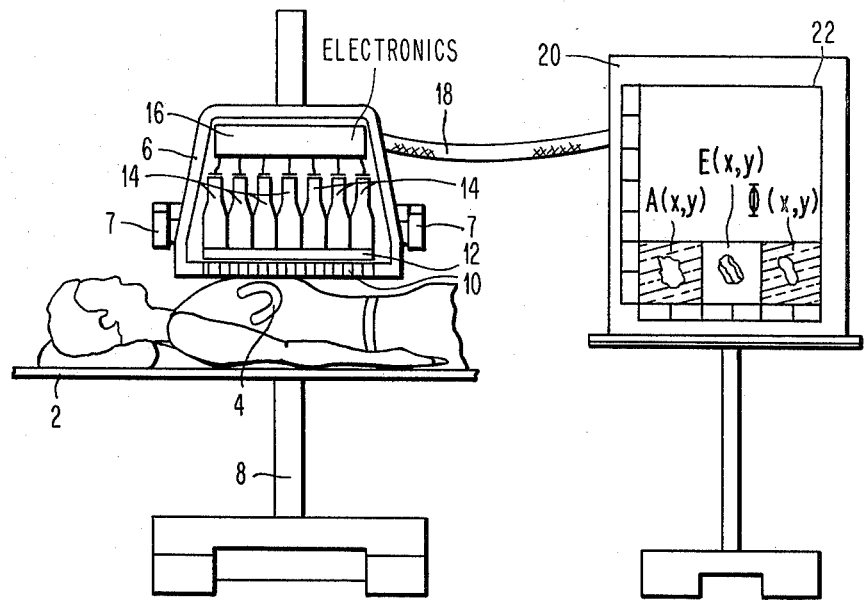
FIG. 1 is an overview of a cardiac imaging apparatus incorporating a gamma camera.

With reference to FIG. 1, a patient who has received a radiotracer is supported by a table top 2. The ma camera 6 supported by arms 7 and by a stand 8 is brought close to the patient's chest. Photons resulting from the decay of the radiotracer pass through the collimator 10 of the radiation detector head 6. They enter a scintillator crystal 12 which, for instance, may consist of sodium iodide activated with thallium. In the scintillator crystal 12, each arriving gamma photon interacts to cause a flash of light. This flash of light is detected by an array of photomultiplier tubes 14. The resulting signal is preamplified and transmitted to scintillation camera electronics 16. These electronics 16 contain conventional position circuitry where the location x, y of the interaction with the scintillator crystal 12 is determined. An electric process signal identifying the location x, y of each interaction is sent, via a cable 18, to a computer system 20 where it is stored.

The computer system 20 in a well-known manner forms and stores a time-activity curve c(t) for each location or pixel. The process signal may be displayed on a screen 22 which is associated with the computer system 20. When the signals from a series of interactions have been processed and displayed, the pixel formation forms a nuclear image.

In the present case, three specific images are obtained additionally. These images are designated by A(x,y), E(e,y), and $\phi$(x,y). The images A(x,y), E(x,y) and $\phi$(x,y) take up only a comparatively small portion of the whole screen 22. The larger portion of the screen 22 is used for the display of other information.

Figure 2:
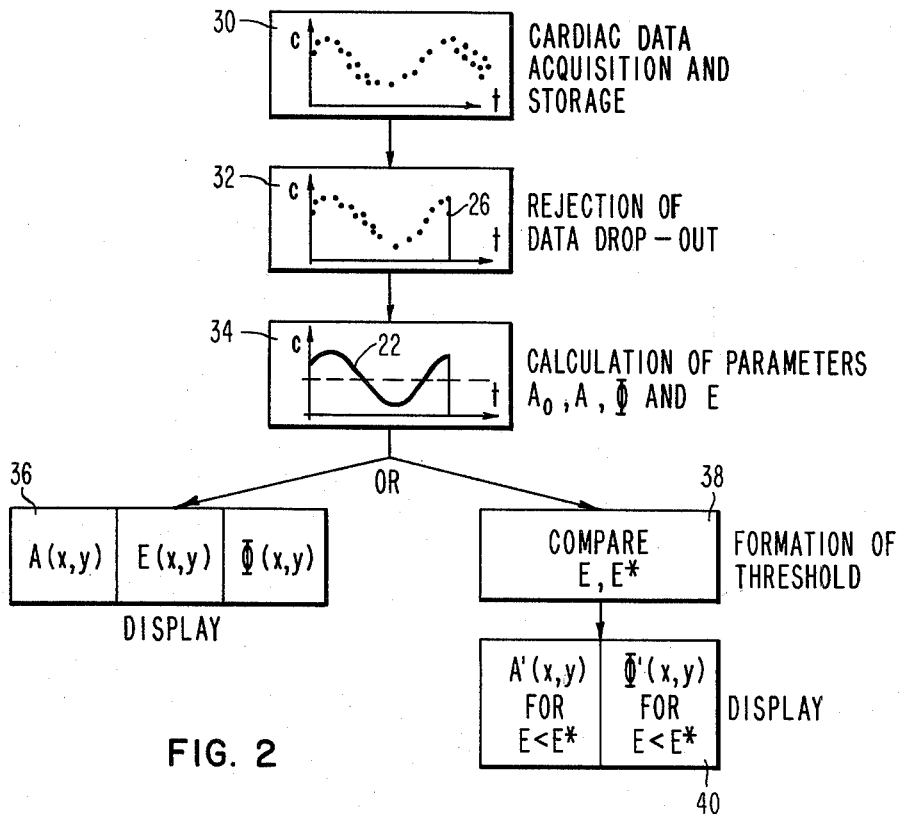
FIG. 2 is a flow chart illustrating processing of data acquired by the gamma camera.

In FIG. 2 the processing of the electric signals obtained from the electronics 16 is illustrated. In the memory of the computer 20, a time-activity curve c(t) is formed for each location x, y of the crystal 12 or, correspondingly, for each pixel on the screen. The time-activity curve c(t) is the radiation count c as a function of time t. The acquisition of radionuclide sineangiograms is a standard procedure and well known to those skilled in the art. Therefore, it does not have to be explained in more detail. The time-activity c(t) is a sinusoidal function as can best be seen in FIG. 3.

Figure 3:
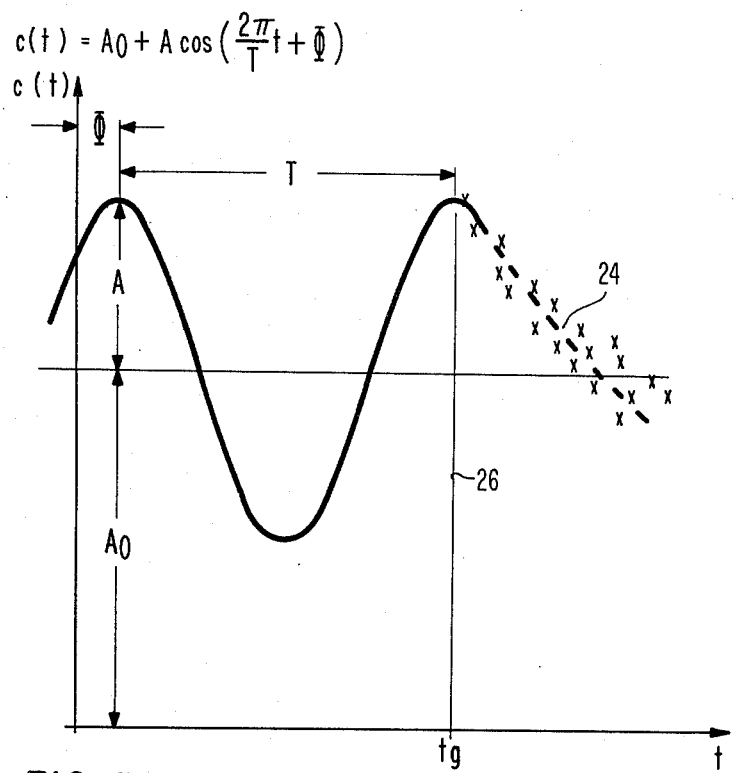
FIG. 3 is a time-activity curve wherein radionuclide counts are plotted versus time.

As mentioned before, the sinusoidal functions, that is the time-activity curves c(t) of all pixels, are stored in the matrix of the memory of the computer 20. Subsequently, a radionuclide cineangiography study and a diagnosis of the cardiac images can be performed. The time-activity curves c(t) are also used for other purposes, as will be explained in the following:

As can be seen in FIG. 3, each acquired time-activity curve c(t) is fitted to a cosine wave of the form $$c(t) = A_o + A \cos(2\pi t/T + \phi). \tag{2}$$

Herein $A_o$ is the average value of the fit or the zero frequency amplitude, A is the amplitude of the cosine wave, T is the period of the cosine wave, and $\phi$ is the phase of the cosine wave c(t). The four parameters that may be varied during the fit are $A_o$, A, T and $\phi$.

Preferably, a standard mathematical technique known as "least square fitting" is applied to fit the time-activity curves c(t) of the individual pixels to cosine functions $A_o + A \cos(2\pi t/T + \phi)$. The "least square fitting" technique renders good results even if only partial-cycle data can be used. There is no restriction on the number of data points used. In addition, the position in time of the fitted points is arbitrary, e.g. the last portion of the cycle may be ignored.

One procedure is as follows: The T and $\phi$ parameters are nonlinear and can be found by a search procedure. After the values for T and $\phi$ are chosen, the $A_o$ and A parameters are found with a linear fitting procedure. The value $A_o$ is the average value of the pixel counts. The parameter A indicates the amount or amplitude of motion of the pixel. The parameter $A_1$ indicates the amount or amplitude of motion of the pixel. The parameter $\phi$ is the phase of the pixel motion and indicates the "time of onset of contraction" of the pixel. The parameter T which is the fundamental period of the pixel motion is proportional to the velocity of contrac- tion.

Assuming that the value T is fixed, the parameter values for each pixel may be found by the following procedure:

1. Choose a value for the phase $\phi$.
2. Find the values of $(A_o + A)$ which best fit the curve c(t) by a linear least square fitting (LSF) technique.
3. Repeat for a number of values of $\phi$ until the best fit to the data is found as determined by the LSF technique.

Sine functions may also be fit to the data c(t) in place of the cosine functions. The results differ from cosine fits only by a phase angle of 90°.

An alternate form of the sinusoidal function used to fit the pixel time-activity curves c(t) is:

$$c(t) = A_o a_R \cos \omega t + a_I \sin \omega t, \tag{3}$$

where $\omega = 2\pi/T$ is the frequency and $a_R$ and $a_I$ are amplitudes. R and I stand for R→real, I→imaginary
The equation (3) is equivalent to equation (2) if one makes the identification:

$$A = \sqrt{a_R^2 + a_I^2}$$

$$\phi = \tan^{-1}\left(\frac{a_I}{a_R}\right)$$

When this functional form is used in the least square fitting procedure, three equations result containing three unknowns $A_o$, $A$, and $\phi$. In addition, the equations are linear in these parameters which means that they are solvable by a simple matrix inversion technique.

The techniques identified above are superior to a Fourier analysis routine and allow partial cycles to be analyzed. They provide superior assessment of amplitude and phase in arrhythmic patients.

The period I, although not a fitted parameter in the presently suggested technique, may be varied arbitrarily and may also become a fitted parameter. This allows the fitting procedure to use the "natural" heart period and not necessarily the R—R interval. A bonus gained from this last point is that more of the motion information contained in the pixel time activity curve c(t) is concentrated in the fundamental period T and not shared with higher frequency components. Based on studies, it has been found that a good value for the period T is, e.g. 500 msec.

As a result of each fitting, a smooth curve 22 of sinusoidal character is obtained. The values $A_0$, $A_1$, T and $\phi$ parameterize the motion of individual pixels in the intended cardiac nuclear medicine blood pool study.

To repeat:

During the fitting procedure for each pixel location (x,y), three parameters are calculated and stored for further use. These three parameters contain essentially all the useful information necessary to quantify heart motion from a radionuclide cineangiographic study. These parameters are the zero frequency amplitude $A_0$, the phase $\phi$ and the amplitude A of the fundamental frequency of the heart cycle. In addition, an error value E is extracted from the fitted cosine wave c(t). This error value E represents the reliability of the acquired time-activity curve c(t). Details of the extraction of the error value E will be explained in detail later.

It has been observed that at the trailing edge of curve 22, a so-called data drop-out 24 occurs, see FIG. 3. This is due to the RR interval variation. The data drop-out 24 contributes to the observation that the interpolation of the curve 22 is frequently not very reliable. In other words, it has been determined that the data $A_0$, A and $\phi$ are not very accurate due to the data drop-out 24 at the end of the curve c(t). In order to increase the accuracy, in the present fitting procedure there is performed a "cut-off" of the data drop-out 24. This is indicated in FIG. 3 by a vertical line 26 going through the last maximum of the curve c(t) at the point of time $t_g$. That means that data beyond the time limit $t_g$ are ignored in the calculation of the parameters $A_0$, A and $\phi$. This clearly eliminates errors which might be otherwise caused by the trailing portion 24 of the curve 22.

Turning back to FIG. 2, it will be noted that after the data acquisition and storage (see block 30), after the rejection of the data drop-out 24 (see block 32) and after the calculation of the parameters $A_0$, A, $\phi$, and E (see block 34), the quantities A and $\phi$ are plotted in gray scale in the places of the pixel coordinates x,y. Thus, images A(x,y) and $\phi$(x,y) result (see block 36) which summarize the regional cardiac motion. The image A(x,y) may be termed a first functional image or amplitude image which is indicative of the amount of a movement of the cardiac structure 4. The image $\phi$(x,y) may be termed a second functional image or phase image. It is indicative of the point of time when the pixels of the cardiac structure perform a movement. Both images A(x,y) and $\phi$(x,y) are displayed for diagnostic evaluation of regional cardiac wall motion.

Even though the amplitudes A of the fundamental frequency of the heart cycle and the phases $\phi$ imaged for all pixels are valuable tools in evaluating the amount of heart motion and the point of time when such motion occurs, there is no indication for the observing physician as to how reliable these parameters A and $\phi$ really are. In order to overcome this problem, according to a first possibility the error image E(x,y) may be displayed directly on the screen 22, see block 36 in FIG. 2. This error image E(x,y) may be displayed next to the images A(x,y) and $\phi$(x,y). It is a third functional image which is indicative of the reliability of the individual amplitude and phase values contained in the first and second image, respectively.

Each individual error value E(x,y) may be calculated from the parameters $A_0$(x,y) and A(x,y) according to $$E(x,y) = \sqrt{2/N_F} \ \sqrt{A_0(x,y)} \ /A(x,y), \qquad (4)$$

wherein $N_F$ is the number of the fitted frames, $A_0$ is the average value of the fit and A is the amplitude of the fit. The unit of the error value E obtained according to equation (4) is radian. If the unit is to be in degree, a factor 180°/$\pi$ has to be applied.

It should be mentioned that the blocks 30 to 34 in FIG. 2 may represent a computer that performs the indicated functions.

Figure 4:
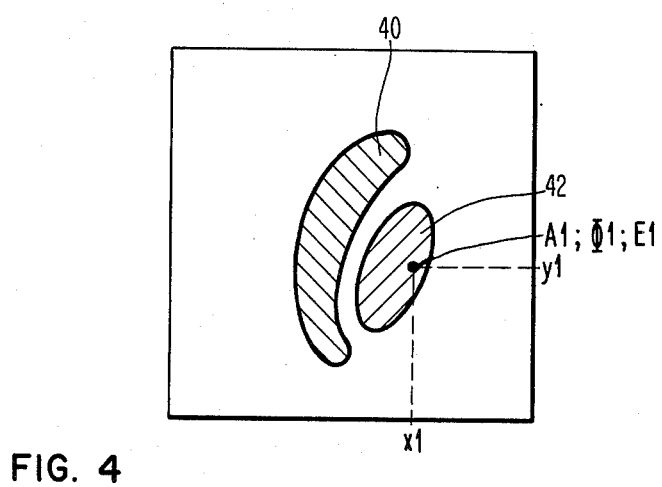
FIG. 4 is a diagram illustrating an amplitude image, a phase image, and an error image of a cardiac structure.

The composition of all three images A(x,y), E(x,y) and $\phi$(x,y) can be depicted from FIG. 4, where a specific pixel location xl, yl is contemplated. The right heart ventricle is designated by 40, and the left heart ventricle is designated by 42. It is assumed that the contemplated pixel lies in the left heart ventricle 42. The least square fitting of the associated time-activity curve provides an image amplitude Al, a phase value $\phi$1, and an error value E1.

In FIG. 2 is also demonstrated a second possibility of how error values E(x,y) may be used to form an image representing the reliability of the calculated data A and $\phi$. According to block 38, each of the error values E is compared with a predetermined maximum error value E*. This block 38 may also be implemented by the aforementioned computer. Of interest are only those data A and $\phi$ for which the calculated error value E is smaller than the predetermined maximum error value E*. Thus, for each location x,y the parameters A and $\phi$ are only displayed when this error condition E<E* is observed. All other parameters A and $\phi$ are not displayed. Consequently, images A'(x,y) and $\phi$'(x,y) are displayed which contain only reliable data. This is indicated in FIG. 2 in the block 40.

The afore-mentioned fitting procedure may be used in monitoring and controlling the data acquisition process on a scintillation camera system containing a computer such as the model "SCINTIVIEW" produced by Siemens Gammasonics, Inc., Des Plaines, Ill. The operator may set a desired phase resolution before or during the study by entering a corresponding value into the memory of the system or on external switches which the program may access. Since the phase resolution depends on the amplitude and average value of the curve being fitted, the phase and its expected error for each pixel in a region of interest should be periodically updated. The data acquisition may be terminated by the program when the desired phase resolution is reached for every pixel in the region of interest. A table of phase resolutions as a function of amplitude and average value may be resident in the memory of the scintillation camera system.

While the form of the method and apparatus for cardiac nuclear imaging herein described consitutes preferred embodiments of the invention, it is to be understood that the invention is not limited to the preceise forms, and that a variety of changes may be made therein without departing from the scope of the invention.

What is claimed is:

1. A method for displaying images of a cardiac structure in nuclear examinations, comprising the steps of
    (a) acquiring cardiac data in accordance with the local distribution (x,y) of a radiolabeled tracer in said cardiac structure, each of said data representing a time-activity curve (c(t)) at a location (x,y) of a pixel matrix positioned over said cardiac structure, whereby said time-activity curves(c(t)) are radiation counts (c) as a function of time (t);
    (b) storing said acquired cardiac data;
    (c) fitting each acquired time-activity curve (c(t)) to a cosine wave of the form $$c(t) = A_o + A \cos\left(\frac{2\pi}{T} t + \phi\right),$$

wherein $A_o$ is the average value of said fitted cosine wave (c(t)), wherein A is the amplitude of said cosine wave (c(t)), wherein T is the period of said cosine wave (c(t)), and wherein $\phi$ is the phase of said cosine wave (c(t));
    (d) extracting from said fitted cosine wave (c(t)) said amplitude (A), said phase ($\phi$) and an error value (E), whereby said error value (E) represents the reliability of said acquired time-activity curve (c(t)); and
    (e) displaying for each location (x,y) simultaneously
        (e1) said amplitude (A), thereby obtaining a first functional image (A(x,y)) indicative of the amount of a movement of said cardiac structure;
        (e2) said phase ($\phi$), thereby obtaining a second functional image ($\phi$(x,y)) indicative of the point of time when portions of said cardiac structure perform a movement; and
        (e3) said error value (E), thereby obtaining as a third functional image (E(x,y)) an error image which is indicative of the reliability of said individual amplitude and phase values contained in said first and second functional image, respectively.

2. A method for displaying images of a cardiac structure in nuclear examinations, comprising the steps of
    (a) acquiring cardiac data in accordance with the local distribution (x,y) of a radiolabeled tracer in said cardiac structure, each of said data representing a time-activity curve (c(t)) at a location (x,y) of a pixel matrix positioned over said cardiac structure, whereby said time-activity curve (c(t)) are radiation counts (c) as a function of time (t);
    (b) storing said acquired cardiac data;
    (c) fitting each acquired time-activity curve (c(t)) to a cosine wave of the form $$c(t) = A_o + A \cos\left(\frac{2\pi}{T} t + \phi\right),$$

wherein $A_o$ is the average value of said fitted cosine wave (c(t)), wherein A is the amplitude of said cosine wave (c(t)), wherein T is the period of said cosine wave (c(t)), and wherein $\phi$ is the phase of said cosine wave (c(t));
    (d) extracting from said fitted cosine wave (c(t) said amplitude (A), said phase ($\phi$) and an error value (E), whereby said error value (E) represents the reliability of said acquired time-activity curve (c(t));
    (e) comparing said error value (E) with a predetermined maximum error value (E*); and
    (f) displaying for each location (x,y) a parameter (A,$\phi$) extracted from said fitted cosine wave (c(t)) when said error value (E) is smaller than said predetermined maximum error value (E*).

3. The method according to claim 1 or 2, wherein said error value (E) is calculated according to $$E = \sqrt{2/N_F} \; \sqrt{A_o} \; /A_1$$

wherein
    $N_F$ is the number of fitted frames,
    $A_o$ is the average value of the fit,
    $A_1$ is the amplitude of the fit,
and wherein the unit of the error value E is radian.

4. The method according to claim 1 or 2, wherein said acquired time-activity curve (c(t)) contains a data drop-out at its trailing edge, further comprising the step of eliminating said data drop-out when fitting said acquired time-activity curve (c(t)) to said cosine wave.

5. An apparatus for displaying images of a cardiac structure in nuclear examinations, comprising
    (a) a gamma camera for acquiring cardiac data in accordance with the local distribution (x,y) of a radiolabeled tracer in said cardiac structure, each of said data representing a time-activity curve (c(t)) at a location (x,y) of a pixel matrix positioned over said cardiac structure, whereby said time-activity curve (c(t)) are radiation counts (c) as a function of time (t);
    (b) storage means operatively connected to said gamma camera for storing said acquired cardiac data;
    (c) calculation means
        (c1) for fitting each acquired time-activity curve (c(t)) to a cosine wave of the form $$c(t) = A_o + A \cos\left(\frac{2\pi}{T} t + \phi\right),$$

wherein $A_o$ is the average value of said fitted cosine wave (c(t)), wherein A is the amplitude of said cosine wave (c(t)), wherein T is the period of said cosine wave (c(t)), and wherein φ is the phase of said cosine wave (c(t)); and (c2) for extracting from said fitted cosine wave (c(t)) said amplitude (A), said phase (φ) and an error value (E), whereby said error value (E) represents the reliability of said acquired time-activity curve (c(t)); and (d) at least one display device for displaying for each location (x,y) simultaneously (d1) said amplitude (A), thereby obtaining a first functional image (A(x,y)) indicative of the amount of a movement of said cardiac structure;

(d2) said phase (φ), thereby obtaining a second functional image (φ(x,y)) indicative of the point of time when portions of said cardiac structure perform a movement; and (d3) said error value (E), thereby obtaining as a third functional image (E(x,y)) an error image which is indicative of the reliability of said individual amplitude and phase values contained in said first and second functional image, respectively.

6. An apparatus for displaying images of a cardiac structure in nuclear examinations, comprising (a) a gamma camera for acquiring cardiac data in accordance with the local distribution (x,y) of a radiolabeled tracer in said cardiac structure, each of said data representing a time-activity curve (c(t)) at a location (x,y) of a pixel matrix positioned over said cardiac structure, whereby said time-activity curve (c(t)) are radiation counts (c) as a function of time (t);

(b) storage means operatively connected to said gamma camera for storing said acquired cardiac data;

(c) calculation means (c1) for fitting each acquired time-activity curve (c(t)) to a cosine wave of the form $$c(t) = A_o + A \cos\left(\frac{2\pi}{T} t + \phi\right),$$

wherein $A_o$ is the average value of said fitted cosine wave (c(t)), wherein A is the amplitude of said cosine wave (c(t)), wherein T is the period of said cosine wave (c(t)), and wherein φ is the phase of said cosine wave (c(t));

(c2) for extracting from said fitted cosine wave (c(t)) said amplitude (A), said phase (φ) and an error value (E), whereby said error value (E) represents the reliability of said acquired time-activity curve (c(t)); and (c3) for comparing said error value (E) with a predetermined maximum error value (E*); and (d) display means for displaying for each location (x,y) a parameter (A,φ) extracted from said fitted cosine wave (c(t)) when said error value (E) is smaller than said predetermined maximum error value (E*).

* * * * *